(12) United States Patent
Walters

(10) Patent No.: US 10,449,225 B1
(45) Date of Patent: Oct. 22, 2019

(54) **ALLEVIATING GASTROINTESTINAL DISTRESS USING *COFFEA ARABICA* EXTRACT**

(71) Applicant: Donald L. Walters, Tujunga, CA (US)

(72) Inventor: Donald L. Walters, Tujunga, CA (US)

(*) Notice: Subject to any disclaimer, the term of this patent is extended or adjusted under 35 U.S.C. 154(b) by 0 days.

(21) Appl. No.: 15/932,993

(22) Filed: Jun. 7, 2018

Related U.S. Application Data

(63) Continuation of application No. 15/530,600, filed on Feb. 6, 2017, now abandoned.

(60) Provisional application No. 62/494,840, filed on Aug. 22, 2016.

(51) Int. Cl.
*A61K 36/00* (2006.01)
*A61K 36/74* (2006.01)
*A61K 31/216* (2006.01)

(52) U.S. Cl.
CPC ............ *A61K 36/74* (2013.01); *A61K 31/216* (2013.01)

(58) Field of Classification Search
None
See application file for complete search history.

(56) References Cited

U.S. PATENT DOCUMENTS

| | | | |
|---|---|---|---|
| 7,691,828 B2 | 4/2010 | Shioya et al. | 514/54 |
| 7,790,205 B2 | 9/2010 | Tripp et al. | 424/725 |
| 8,246,943 B2 | 8/2012 | Banerjee et al. | 424/78.37 |
| 8,257,754 B2 | 9/2012 | Tripp et al. | 424/725 |
| 8,557,306 B2 | 10/2013 | Tripp et al. | 424/725 |
| 8,716,351 B1 | 5/2014 | Huang et al. | 514/714 |
| 2004/0178495 A1 | 9/2004 | Yean et al. | 424/616 |

FOREIGN PATENT DOCUMENTS

TW 201113015 A1 4/2011

OTHER PUBLICATIONS

Molska et al, Effect of coffee extract (*Coffea arabica*) in two animal models of Parkinson's disease. Society for Neuroscience Abstract Viewer and Itinerary Planner, (2010) vol. 40. Meeting Info.: 40th Annual Meeting of the Society-for-Neuroscience (Year: 2010).*
Ponepal, Use of a Coffea arabica tosta extract for the prevention and therapy of polyfactorial infectious diseases innewborn calves. DTW. Deutsche tierarztliche Wochenschrift, (Oct. 1996) vol. 103, No. 10, pp. 309-314. (Year: 1996).*
Tripathi et al, Method development and validation for quantification of chlorogenic acid in Coffea arabica extract using high performance liquid chromatography. Der Pharmacia Lettre (2014), vol. 6, No. 6, pp. 89-92 (Year: 2014).*

* cited by examiner

*Primary Examiner* — Qiuwen Mi
(74) *Attorney, Agent, or Firm* — Chris Whewell

(57) ABSTRACT

Provided are compositions useful as dietary supplements for the relief of unstable gastrointestinal symptoms such as constipation and diarrhea and methods of using same. The compositions consist essentially of the extract of the fruits of *Coffea arabica*, in combination with other materials recognized by those skilled in the art as being useful secondary ingredients in a composition for oral administration. The secondary ingredients do not affect the basic properties conferred by the presence of the extract of *Coffea arabica*, The extract of *Coffea arabica* is present in compositions according to the disclosure in relatively high amounts, and the compositions are devoid of any dietary fiber other than that incidental in the extracts, and are free from any added alginic acids or their salts. Methods according to the disclosure are described, which involve daily oral administration of the compositions described prior to mealtime.

12 Claims, No Drawings

ALLEVIATING GASTROINTESTINAL DISTRESS USING *COFFEA ARABICA* EXTRACT

TECHNICAL FIELD

This invention relates generally to uses of compositions of matter for the purpose of alleviating gastrointestinal distress, and to combinations including the compositions. In one narrower aspect, it relates to compositions useful for alleviating or preventing certain symptoms associated with Irritable Bowel Syndrome ("IBS"), which presents with symptoms of colitis, diarrhea and constipation, general stomach malaise, including diabetic constipation. Symptoms of IBS-C (constipation), IBS-D (diarrhea) and IBS-M (mix of C and D), and gastroesophageal reflux disease ("GERD"), commonly referred to as heartburn, acid reflux, or acid indigestion, are alleviated by methods herein using the compositions described.

BACKGROUND OF THE INVENTION

Various compositions and materials have been proffered in the past as being beneficial in the treatment, alleviation, and prevention of various gastrointestinal conditions, including IBS, diarrhea and others. One material in popular use is loperamide, sometimes sold under the trade name IMMODIUM® AD. Other materials asserted for these uses include various compositions containing polyphenols, soluble fiber, and anti-microbial materials such as glyceryl monolaurate. However, none so far have successfully restored stability to the function of the human gastrointestinal tract using the benign natural plant extract of this disclosure as its active component. The present invention provides compositions consisting essentially of such a material.

SUMMARY OF THE INVENTION

Methods are provided for restoring stability to the function of the human gastrointestinal tract by providing relief from a symptom selected from the group consisting of: constipation, diarrhea, colitis, IBS (irritable bowel syndrome), general stomach malaise and GERD. The methods comprise administering to a human subject a composition consisting essentially of an extract of the raw fruits of *Coffea arabica*, the extract being present in the composition in any amount between 50% by weight and 99% by weight based on the total weight of the composition. A typical amount of composition administered as a dietary supplement is any amount between 500 milligrams and 1500 milligrams for a single dose or supplementation event, with about 800 milligrams being typical for an adult weighing between 130 and 200 pounds.

Compositions are also provided, which are useful for restoring stability to the function of the human gastrointestinal tract by alleviating a condition selected from the group consisting of: colitis, irritable bowel syndrome, general stomach malaise, diarrhea, and constipation. The compositions consist essentially of an extract of the raw fruits of *Coffea arabica*, the extract being present in said composition in any amount between 50% by weight and 99% by weight based on the total weight of the composition.

DETAILED DESCRIPTION

This disclosure concerns the berries of the plant known as *Coffea arabica* and beneficial effects relating thereto from its ingestion. In particular, extracts of the berries of *Coffea arabica* provide a material useful in accordance with the present disclosure, and particularly the un-roasted, or as-harvested berries or fruits, which are sometimes referred to as raw "coffee beans." Some embodiments of the invention only concerns the berries of *Coffea arabica* and excludes all other species of coffee fruits or beans for the uses taught herein. As used herein, "*Coffea arabica* extract" means an extract of the berries of the plant *Coffea arabica*, whether as obtained from an extraction process or modified as described herein.

An extract of *Coffea arabica* useful herein in some embodiments according to this disclosure is provided by first picking ripe, mature, or immature berries from the *Coffea arabica* plant. The beans, or any other parts of the plant when selected to be employed, can be dried and ground if desired or employed as-harvested in an extraction process.

An extraction process useful for providing an extract of *Coffea arabica* useful in accordance with this disclosure is in some embodiments a solvent extraction process. In some embodiments the solvent is water. In other embodiments the solvent is mineral oil. In other embodiments, the solvent is any glycerol-based ester oil including without limitation any vegetable oils known to those skilled in the art. In further alternate embodiments, the solvent can be a mixture of water with any one or more than one C1-C4 alcohol, straight-chain or branched, in any selected proportion of water and the alcohol(s). The solvent extraction process can be a batch process or a continuous process as known by those of ordinary skill in the art, including percolation and soxhlet extraction procedures, carried out at any selected temperature and pressure. In some embodiments the temperature at which the extraction is conducted is room temperature. In some embodiments, the solvent is supercritical carbon dioxide.

In some embodiments, an extract of *Coffea arabica* is commercially available and can be used in a composition and method according to this disclosure. One such exemplary extract is marketed as "50% chlorogenic acid *Arabica* Bean Fruit Extract Powder, sold by QC Unlimited, d.b.a. Prescribed For Life™ of 1406 E. Main Street, Fredericksburg, Tex. which is a standardized extract that has been standardized so that it contains 50% chlorogenic acid content by weight. In some embodiments the extract of *Coffea arabica* useful herein can be re-crystallized from a polar solvent such as ethanol. In other embodiments, the extract is non-crystalline or amorphous. In alternate embodiments, the extract of *Coffea arabica* is a gummy residue. All of these forms of extract of *Coffea arabica* are suitable for use in accordance with the present disclosure. Sometimes such extracts are referred to as "green coffee bean extract."

From an extract(s) of *Coffea arabica*, compositions according to some embodiments of this disclosure are prepared by mixing such extract(s) with various other materials, as desired or selected to be present. In some embodiments the *Coffea arabica* extract is ground with a mortar or otherwise pulverized, co-comminutated and/or combined with or formulated into a final formulation suitable for oral administration which can comprise a friable pill, capsule, bolus or the like. In some embodiments the concentration of *Coffea arabica* extract in the final formulation is any amount between about 30% by weight and about 95% by weight based on the weight of the final formulation, including all weight percentages and ranges of weight percentages therebetween. In some embodiments the *Coffea arabica* extract is blended with at least one other material that is a solid or liquid at room temperature, in any amount, in order to provide an extract concentrate. Such at least one other material in some embodiments comprises a material selected from the group consisting of: silicates, aluminosilicates and silica present in effective flow-enhancing amounts to enable the crystalline extract to flow freely when poured.

Crystalline or other *Coffea arabica* extracts as described and/or provided herein may be further refined to isolate or concentrate any one, or more than one, of the compounds present in the *Coffea arabica* extract using methods or techniques generally known to those skilled in the art.

A *Coffea arabica* extract provided according to some embodiments of the disclosure contains at least any one compound, and in other embodiments contains any mixture comprising a plurality including any two or any number more than two compounds present in this constituent listing now set forth, the compounds in such listing comprising: 2,3-butanedione; Pentanal; Methyl 3-methylbutanoate; 2,3-pentanedione; Hexanal; 2-Methyl-2-butenal; (E)-3-Penten-2-one; 2-heptanone; heptanal; 3-Methyl-2-butenal; 3-Methyl-1-butanol; 2-Methyl-1-butanol; 2-Pentylfuran; Dihydro-2-methyl-3(2H)-furanone; 3-Hydroxy-2-butanone; 3-Methyl-2-buten-1-ol; 2-Heptanol; 1-Hexanol; 6-linalool oxide; 1-Octen-3-ol; Furfural; trans-Linalool oxide; 1H-pyrrole; Benzaldehyde; 2-Isoburyl-3-methoxypyrazine; (E)-2-Noneal; Linalool; 1-Butyrolactone; Phenylacetaldehyde; 2-Furanmethanol; 2-Methylbutanoic acid; 3-Methylbutanoic acid; α-Terpineol; Naphthalene; Methyl salicylate; (E,E)-2,4-Decadienal; (E)-1-Damascenone; Hexanoic acid; Geranylacetone; Benzyl alcohol; 2-Phenylethanol; *Coffea arabica* diterpenes; cafestol; methylated forms of cafestol; kahweol; methylated forms of kahweol; 2-Acetylpyrrole; 2,6-Dimethylnaphthalene; Eugenol; Octanoic acid; (Z)-Isoeugenol; Nonanoic acid; p-Vinylguaiacol; Methyl palmitate; Megastigmatrieone I; Megastigmatrienone II; p-Vinylphenol; 1H-Indole; Methyl oleate; Methyl linoleate; Myristic acid; Plamitic acid; Caffeine; Stearic acid; Oleic acid; Linoleic acid; chlorogenic acid; esters of chlorogenic acids at the hydroxyl of carbon-1 of the quinic acid portion of the molecule, including (1S, 3R, 4R, 5R)-3-{[(2E)-3-(3,4-Dihydroxyphenyl) prop-2-enoyl]oxy}-1, 4, 5 trihydroxycyclohexane carboxylic acid; caffeoylquinic acids; soluble fiber in the form of high molecular weight polysaccharides; galactomannans; type II arabinogalactans; dicaffeoylquinic acids; feruloylquinic acids; p-coumaroylquinic acids; caffeoyl-feruloylquinic acids; acyl dicaffeoylquinic acids, dimethoxycinnamoylquinic acids, caffeoyl-dimethoxycinnamoylquinic acids, diferuoylquinic acids, feruloyldimethoxycinnamoylquinic acids, sinapoylquinic acids, sinapoyl-caffeoylquinic acids, sinapoyl-feruloylquinic acides, feruloyl-sinapoylquinic acids, including acids described within the metes and bounds of the definitions below. Some of the foregoing chlorogenic acids are represented by the structure:

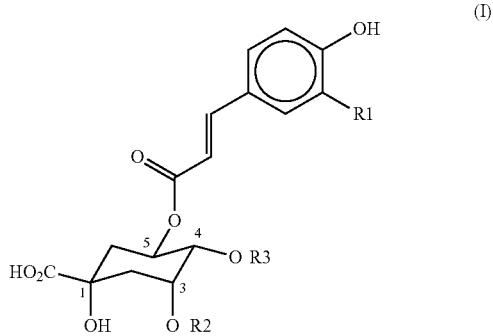

(I)

in which the rest, R1, is selected from the group consisting of: hydrogen, hydroxyl, methoxy, and any C2-C12 alkyl group, whether straight chain, branched, aromatic or aliphatic, including any C2-C12 alkylaromatic groups. When R1 in the above structure is hydroxyl, the structure can be considered a caffeoylquinic acid. When R1 in the above structure is methoxy, the structure can be considered a feruloylquininc acid. When R1 in the above structure (I) is hydrogen, the structure can be considered a para-coumaroylquinic acid.

In the structure (I) above, R2, and R3 are each independently selected from the group consisting of: hydrogen, ferulic acid, and caffeic acid, while the moieties for R in structure (I) above can each be any hydrogen, hydroxyl or methoxy group independently of the selection of R2, and R3 in the quinic acid portion of the chlorogenic acid. In some embodiments, additional trans-cinammic moieties having an R1 within the foregoing definition are attached to the quinic acid ring in the R2 and R3 positions, which R2 and R3 can thus accordingly independently be any feruloylquinic, caffeoylquinic and para-coumaroylquinic acids, to give say, a dicaffeoylquinic acid, as those of ordinary skill in the art readily recognize.

As concerns any of the compounds in the constituent list which are acids or which have an acid form, the present disclosure includes the presence of such materials in their neutralized forms, and in alternate embodiments their esterified forms condensed with any C1 to C24 alcohol. For those component compounds in the listing having a carboxylic acids function, the present disclosure includes the presence of such materials in their anionic forms, including without limitation their alkali metal salts, alkaline earth salts, ammonium salts and substituted ammonium salts, the concentration of the anionic forms of such material(s) being present in a composition according to the disclosure in the amounts specified for the acid form of the material(s). In some embodiments the concentration ranges for components present in a composition according to the disclosure are applied based on the weight percent of the anionic form of the material. In some embodiments, the concentration ranges in a composition according to the disclosure are determined based on the weight percent of the salt, including the cation present. Likewise when basic substances are recited, the present disclosure includes the presence of such materials in their protonated forms, the concentration ranges of such materials being present in a composition according to the disclosure in the amounts specified above for the basic form. In some embodiments the concentration ranges for a composition according to the disclosure is determined based on the weight percent of the protonated form of the material present. In some embodiments, the concentration ranges for a composition according to the disclosure is determined based on the weight percent of the protonated form of the material and including its anion present for charge neutrality present.

In some embodiments, all of the materials in the constituent listing are present in a composition according to the disclosure. In other embodiments any one or any number more than one of the materials in the constituent listing are selectively independently omitted from the contents of a composition according to the disclosure, such as by refining a nascent *Coffea arabica* extract for the purpose of removal of one, or any number greater than one, of materials in the above listing present in the extract using techniques known to those skilled in the art. In other embodiments any one or any number greater than one of such components present in the listing may be purified using techniques known to those of ordinary skill in the art. Such techniques include without limitation liquid chromatography, paper chromatography, distillation under reduced pressure, steam distillation, fractional crystallization, aqueous/non-aqueous liquid layer separation extraction and molecular distillation. For example, to remove nitrogenous basic substances the extract material is put up into aqueous solution and made alkaline, and extraction done using $CHCl_3$ to remove amino compounds, the aqueous layer being subsequently re-acidified or neutralized. In one embodiment, ammonia is used to make the material alkaline for purposes of such extraction, which ammonia is subsequently removed after the extraction having been completed by blowing with nitrogen or treatment to reduced pressure. In another embodiment an aqueous extract of *Coffea arabica* is made slightly acidic by addition of aqueous HCl, and extractions are done using ethyl acetate, ether, chloroform, and/or hexanes. Following extraction, the aqueous layer is subjected to reduced pressure and slight heating or a sweep of nitrogen or other inert gas to facilitate removal of excess HCl. In such embodiments, fractions obtained may be further treated to selectively separate or remove component materials present, using techniques known in the art including without limitation such techniques as preparatory chromatography columns, fractional distillation under vacuo, molecular distillation, precipitation and filtration, etc. In further embodiments, one or more than one of any of the above-named components in the constituent listing are produced synthetically or are otherwise acquired or produced, and are subsequently blended with one another to provide a blend that constitutes a synthetic *Coffea arabica* extract that is useful in providing a composition according to the disclosure, such components that are selected to be present each being individually present at levels within the ranges specified herein. Addition of one or any number more than one of a component of *Coffea arabica* extract to a nascent *Coffea arabica* extract provides an extract that is fortified in the added component(s).

In some embodiments at least any chosen two of the component materials in the constituent listing remain or are present in a *Coffea arabica* extract useful for providing a composition according to this disclosure, the component materials being independently present at concentrations within the range of between 0.1% and 80% by weight based on the total weight of the extract, including all percentages and ranges of percentages therebetween. In some embodiments at least any chosen three of the component materials in the constituent listing above remain or are present in a *Coffea arabica* extract useful for providing a composition according to this disclosure, the component materials being independently present at concentrations within the range specified above in such compositions or extracts. In some embodiments at least any chosen four of the component materials in the listing above remain or are present in a *Coffea arabica* extract useful for providing a composition according to this disclosure, the component materials being independently present at concentrations within the ranges specified above in such composition or extracts. In some embodiments at least any chosen five of the component materials in the listing above remain or are present in a *Coffea arabica* extract useful for providing a composition according to this disclosure, the component materials being independently present at concentrations within the range specified above in such compositions or extracts.

This disclosure includes the use of *Coffea arabica* extracts from which some of the components in the listing above have been removed, and also *Coffea arabica* extracts comprising a plurality of the materials in the listing above which are produced by combining previously-isolated purified component materials from such listing, as well as *Coffea arabica* extracts which are fortified to contain any one or any number more than one of the compounds in the constituent listing at concentrations greater than they were or are present in a nascent *Coffea arabica* extract. For clarity, a nascent *Coffea arabica* extract is the product material extracted from the berries of *Coffea arabica* as it exists following subjecting the berries to an extraction process.

In some embodiments, it is generally desirable for control purposes to employ an extract of *Coffea arabica* that is a standardized extract. One level of standardization that is useful is when the extract is standardized to contain 50% or about 50% (plus or minus 5% in some embodiments) total chlorogenic acid or chlorogenic acids content, in different embodiments. However, extracts standardized to contain at least 30% total chlorogenic acid or chlorogenic acids in different embodiments are also useful herein, as well as extracts having a total chlorogenic acid or chlorogenic acids content between 25% and 70%.

For some embodiments of the disclosure in which it is intended that a *Coffea arabica* extract be ingested, a pharmaceutically-acceptable carrier can be present in a formulation for such use. "Pharmaceutically-acceptable carrier" is used in its ordinary sense herein, generally including pharmaceutically-acceptable, non-toxic diluents, flow improvers, anti-caking agents or other secondary ingredients or materials known by those skilled in the art as being useful in formulation of pharmaceutical compositions for oral administration to human or any other mammalian subjects, which can include also vitamins, minerals and nutrients when the compositions are intended as dietary supplements in some embodiments. Pharmaceutically-acceptable carriers can include, without limitation, one or more than one material selected from the group consisting of buffering agents, solubilizing agents, vitamins, herbal extracts, minerals, stabilizing agents, binders, liquids such as water, saline solution, glycerol and ethanol. Such carriers often facilitate a pharmaceutical composition to be formulated as tablets, pills, dragees, capsules, liquids, gels, syrups, slurries, suspensions, emulsions, and the like for ingestion. A discussion of pharmaceutically-acceptable carriers is available in Remington's Pharmaceutical Sciences (Mack Pub. Co., N.J. 1991).

Other optional ingredients or additives which may be used in combination with *Coffea arabica* extract in formulating compositions according to the present disclosure include pH buffering materials including various protonated or non-protonated phosphates and carbonates. Sodium hydroxide solutions may also be utilized as an alkaline pH adjusting agent. The pH adjusting chemicals function to neutralize acidic materials in a batch of a formulation that may be present to enhance formulation stability.

*Coffea arabica* extracts are useful as the main active ingredient in compositions according to this disclosure, which compositions in some embodiments further contain materials typically known to and used by those skilled in the art of formulating vitamins and dietary supplements. Such other materials generally do not have an impact on the activity of the active ingredient, and therefore a composition of the present disclosure consists essentially of a *Coffea arabica* extract. That is, other materials may be present in a composition for administration to a human subject according to this disclosure, provided they do not materially affect the basic character of the compositions. For purposes of this disclosure, the words "materials typically known to and used by those skilled in the art of formulation" means without limitation any one, or any combination comprising more than one of materials selected from the group consisting of: sodium silicate, polymers, aloe vera, vitamins, anti-oxidants, carotenoids, herbal extracts, plant extracts, flavonoids, iso-flavones, hormones, alkali sulfates, enzymes, colorants, preservatives, essential oils, and chelating agents, each present when selected in conventionally-used amounts, as known by those skilled in the art of formulating compositions for oral administration.

Below are set forth several examples which shall be interpreted as being exemplary of various embodiments of this disclosure and should not be construed as delimitive hereof. When set forth as *Coffea arabica* extract, such extract is understood in these examples only, to be standardized to 50% by weight of total chlorogenic acid content.

Example I

*Coffea arabica* extract standardized to 50% chlorogenic acid 755 milligrams

Example II

| Composition for oral administration | |
| --- | --- |
| *Coffea arabica* extract standardized to 50% chlorogenic acid | 755 milligrams |
| Oregano oil | 10 milligrams |
| Caprylic acid | 15 milligrams |
| Allicin | 15 milligrams |
| Selenium (as selenite) | 100 micrograms |

The above ingredients are combined, blended, or cocomminutated in the usual manner to provide a powdered mixture, which is subsequently put into capsules or compressed to tablet form.

Example III

Bowel Stability Treatment

A 34 year old male suffering from chronic diarrhea for 30 months, having episodes four to five times per day, ingested two gelatin capsules each containing 800 milligrams of the composition according to Example I daily, one capsule being taken in the morning and one capsule being taken in the evening, each administered dose having been taken 20-30 minutes before eating a meal. After three weeks of such daily dietary supplementation, a marked improvement was noticed by the man of the function of his GI tract. After seven weeks of such daily dietary supplementation, the man reported his gut function had nearly returned to normal. After 12 weeks of such daily dietary supplementation, the man reported that his gut function was back to normal, and has remained so for at least sixteen months afterwards.

Example IV

Bowel Stability Treatment

A 35 year old female suffering from IBS-C (constipation) for 10 years ingested two gelatin capsules each containing 800 milligrams of the composition according to Example I daily, one capsule in the morning and one capsule in the evening, each administered dose being taken about 20-30 minutes before eating a meal. After three weeks of such daily dietary supplementation, a marked improvement was noticed by the woman of the function of her GI tract. After seven weeks of such daily dietary supplementation, the woman reported her gut function had nearly returned to normal. After 12 weeks of such daily dietary supplementation, she reported that her gut function was normal, and has remained so for at least twenty months afterwards.

Example V

IBS (C)

A 50 year old female with type one diabetes suffering from chronic constipation for 35 years ingested two gelatin capsules each containing 800 milligrams of the composition according to example 1 daily, one capsule in the morning and one capsule in the evening, each administered dose being taken about 20-30 minutes before eating a meal. After three weeks of such daily dietary supplementation, a marked improvement was noticed by the women of the function of her GI tract. After seven weeks of such daily dietary supplementation, the women reported her gut function had nearly returned to normal. After 12 weeks of such daily dietary supplementation, she reported that her gut function was normal, and has remained so for at least eighteen months afterwards.

Example VI

IBS (C)

A 64 year old male suffering from chronic constipation and gut pains for 10 years with a very black stinky stool ingested two gelatin capsules each containing 800 milligrams of the composition according to example 1 daily, one capsule in the morning and one capsule in the evening, each administered dose being taken about 20-30 minutes before eating a meal. After three weeks of such daily dietary supplementation, a marked improvement was noticed by the man of the function of his GI tract. After seven weeks of such daily dietary supplementation, the man reported his gut function had nearly returned to normal. After 12 weeks of such daily dietary supplementation, he reported that his gut function was normal, and has remained so for at least thirty months afterwards.

Example VII

IBS (C) and GERD

A 38 year old female suffering from chronic constipation for four years ingested two gelatin capsules each containing 800 milligrams of the composition according to example 1 daily, one capsule in the morning and one capsule in the evening, each administered dose being taken about 20-30 minutes before eating a meal. After three weeks of such daily dietary supplementation, a marked improvement was noticed by the women of the function of her GI tract. After seven weeks of such daily dietary supplementation, the women reported her gut function had nearly returned to normal. After 12 weeks of such daily dietary supplementation, she reported that her gut function was normal, and has remained so for at least four months afterwards.

Example VIII

IBS-M and GERD

A 33 year old female suffering from IBS-M (mix of constipation and diarrhea) for five years ingested two gelatin capsules each containing 800 milligrams of the composition according to example 1 daily, one capsule in the morning and one capsule in the evening, each administered dose being taken about 20-30 minutes before eating a meal. After three weeks of such daily dietary supplementation, a marked improvement was noticed by the women of the function of her GI tract and the absence of GERD. After seven weeks of such daily dietary supplementation, the women reported her gut function had nearly returned to normal. After 12 weeks of such daily dietary supplementation, she reported that her gut function was normal, and has remained so for at least four months afterwards.

Example IX

IBS-C and GERD

A 63 year old male suffering from severe IBS-C (constipation) and GERD, (acid reflux) for eight years ingested two gelatin capsules each containing 800 milligrams of the composition according to example 1 daily, one capsule in the morning and one capsule in the evening, each administered dose being taken about 20-30 minutes before eating a meal and the symptoms ceased the 4$^{th}$ day. After three weeks of such daily dietary supplementation, a marked improvement was noticed by the man of the function of his GI tract. After seven weeks of such daily dietary supplementation, the man reported his gut function had nearly returned to normal. After 12 weeks of such daily dietary supplementation, he reported that his gut function was normal, and remained so for at least 20 months afterward.

The subjects in the examples IV through VII, all responded the same as those subjects in Examples II and III at the three week, seven week, and three month times from their first ingesting the composition of Example I as described.

In some embodiments, a composition according to this disclosure is provided in tablet or capsule forms, each tablet or capsule having any amount of a composition consisting essentially of an extract of the raw fruits of the *Coffea arabica* in the range of between 500 milligrams and 1500 milligrams. Although the examples above provide for administering the dietary supplement herein provided twice per day, the present disclosure also includes methods wherein a subject ingests such amounts of a composition of this disclosure three times per day, and four times per day, or more often as deemed desirable by the person or their physician. In general, the instant compositions do not provide immediate relief from the symptoms alleviated, but rather the administration of the compositions needs to be undertaken over a period of about 12 weeks for a complete restoration of normal bowel or GI tract function, with improvements first being noticed at about three weeks, and another noticeable level of improvement occurring at about seven weeks from initial supplementation. Although not being bound by any particular theory, it is postulated that when practicing a method according to this disclosure, slow changes are caused to occur in the gut flora profile of the subject, which can include altering the relative amounts or populations of various microbes present in the GI tract. The present invention, unlike conventional medicaments or other herbal extracts does not seek a rapid drastic change within the body, but rather produces a slower restoration of normal GI function which is believed to be longer-lived than when using prior art compositions or methods.

Compositions used in methods according to some embodiments of this disclosure do not contain any added dietary fiber. In some embodiments, compositions used in methods according to this disclosure only contain fiber to the extent that it is present in the extract of the *Coffea arabica*. In some embodiments, compositions used in methods according to this disclosure are devoid or substantially devoid of any alginic acids, or salts thereof.

When *Coffea arabica* beans are referred to herein as being green, this means coffee seeds (beans) of *Coffea arabica* fruits that have not been roasted. The roasting process of *Coffea arabica* beans reduces amounts of the chemical chlorogenic acid. Therefore, green *Coffea arabica* beans have a higher level of chlorogenic acid compared to roasted coffee beans.

Although not wishing to be bound by any theory, it is presently believed that the chlorogenic acid in green coffee is an active ingredient of compositions and methods provided herein. In some embodiments, compositions according to this disclosure are devoid of dietary fiber, either soluble or insoluble, as it is believed fiber can interact with chlorogenic acid and render it less effective in the uses described herein, than when no fiber is present in the compositions when taken.

In some embodiments, as used herein, terms such as "consisting essentially of" have their ordinary meaning, which when applied to a composition is deemed as including other materials which do not materially affect the basic and novel characteristics of the composition, or a method using a composition, provided herein. In some embodiments and claims relating thereto which contain the phrase "consisting essentially of", it is not proper for purposes of this specification to interpret such terms as being equivalent with the single word "comprising."

Although this invention has been described and disclosed in relation to various embodiments, modifications, combinations, and alterations of the features of various embodiments disclosed may become apparent to persons of ordinary skill in this art after reading and understanding the teachings of this specification, drawings, and the claims appended hereto. The present disclosure includes subject matter defined by any combinations of any one (or more) of the features, elements, or aspects present described in reference to any embodiment described in this disclosure with one or more feature(s), element(s), or aspect(s) described in relation to any other one (or more) other embodiments described. These combinations include the incorporation of the features and/or aspect(s) of any dependent claim, singly or in combination with features and/or limitations of any one or more than one of the other dependent claims, with features and/or limitations of any one or more than one independent claim(s), with the remaining dependent claims in their original text being read and applied to any independent claim(s) so modified. These combinations also include combination of the features and/or limitations of one or more of the independent claims with features and/or limitations of another one or more than one of the independent claims to arrive at a modified independent claim, with the remaining dependent claims in their original text or alternately as modified per the foregoing, being read and applied to any independent claim(s) so modified.

The invention claimed is:

1. A method for restoring stability to the function of the human gastrointestinal tract by providing relief from any symptom selected from the group consisting of: constipation, diarrhea, and gastroesophageal reflux disease; said method comprising orally administering to a human subject who is suffering from said symptom a composition consisting essentially of an extract of the raw fruits of *Coffea*

*arabica*, said extract being present in said composition in any amount between 50% by weight and 99% by weight, based on the total weight of said composition.

2. A method according to claim 1 wherein the amount of *Coffea arabica* extract in a single administration of said composition is any amount within the range of between 500 milligrams and 1500 milligrams.

3. A method according to claim 2 wherein said administering is undertaken two times daily.

4. A method according to claim 1 wherein said administering is undertaken two times daily for a time period of three weeks.

5. A method according to claim 2 wherein said administering is undertaken two times daily for a time period of seven weeks.

6. A method according to claim 1 wherein said administering is undertaken two times daily for a time period of twelve weeks.

7. A method according to claim 1 wherein said administering is undertaken three times daily.

8. A method according to claim 1 wherein said composition is substantially devoid of alginic acids or salts thereof.

9. A method according to claim 1 wherein said composition is free from fiber, other than that incidental and present in said extract.

10. A method according to claim 1 wherein said extract is standardized to contain 30% of chlorogenic acid.

11. A method according to claim 1 wherein said extract is standardized to contain about 50% of chlorogenic acid.

12. A method for alleviating a human from suffering from constipation, diarrhea, and/or gastroesophageal reflux disease; said method comprising administering an extract of the raw fruits of *Coffea Arabica*, oregano oil, caprylic acid, allicin and selenium, wherein said extract is present in said composition in any amount between 50% by weight and 99% by weight, based on the total weight of said composition to a human in need thereof to effectively treat the constipation, diarrhea and/or gastroesophageal reflux disease.

\* \* \* \* \*